United States Patent
Tisdell et al.

(10) Patent No.: US 6,262,099 B1
(45) Date of Patent: Jul. 17, 2001

(54) 3-(SUBSTITUTED PHENYL)-5-(SUBSTITUTED CYCLOPROPYL)-1,2,4-TRIAZOLE COMPOUNDS

(75) Inventors: Francis E. Tisdell, Carmel; Joe R. Schoonover, Jr., Brownsburg; James T. Pechacek, Indianapolis; Perry V. Ripa, Sun Prairie; Leonard P. Dintenfass; Timothy P. Martin, both of Indianapolis; Donald H. DeVries, Fishers; Mary L. Ash, Zionsville; James M. Gifford, Lebanon; Maurice C. Yap, Zionsville, all of IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/426,077

(22) Filed: Oct. 22, 1999

Related U.S. Application Data

(60) Provisional application No. 60/105,338, filed on Oct. 23, 1998.

(51) Int. Cl.$^7$ ........................ A01N 43/653; C07D 249/08
(52) U.S. Cl. .................... 514/383; 548/267.2; 548/267.4; 548/267.6; 548/267.8; 548/268.6; 548/269.4
(58) Field of Search ........................ 514/383; 548/267.2, 548/267.4, 267.6, 267.8, 268.6, 269.4

(56) References Cited

U.S. PATENT DOCUMENTS

| 5,466,705 | * 11/1995 | Ozaki et al. ..................... 514/383 |
| 5,530,149 | 6/1996 | Scherkenbeck et al. ............ 549/554 |
| 6,015,826 | 1/2000 | Pechacek et al. ................... 514/383 |

FOREIGN PATENT DOCUMENTS

| 217552 | 4/1987 | (EP) . |
| 572142 | 12/1993 | (EP) . |
| 609459 | 2/1994 | (EP) . |
| 8-283261 | 10/1996 | (JP) . |

OTHER PUBLICATIONS

Chemical Abstracts, 126:3095r (1997) abstracting JP 08,245,315.

* cited by examiner

*Primary Examiner*—Patricia L. Morris
(74) *Attorney, Agent, or Firm*—Craig E. Mixan; Donald R. Stuart

(57) ABSTRACT

3-(Substituted phenyl)-5-(substituted cyclopropyl)-1,2,4-triazole compounds are useful as insecticides and acaricides. New synthetic procedures and intermediates for preparing the compounds, pesticide compositions containing the compounds, and methods of controlling insects and mites using the compounds are also provided.

4 Claims, No Drawings

3-(SUBSTITUTED PHENYL)-5-(SUBSTITUTED CYCLOPROPYL)-1,2,4-TRIAZOLE COMPOUNDS

RELATED APPLICATION

This application claims priority from U.S. Provisional Patent Application Ser. No. 60/105,338, filed Oct. 23, 1998.

FIELD OF THE INVENTION

This invention provides new compounds that are useful as insecticides and acaricides, new synthetic procedures and intermediates for preparing the compounds, pesticide compositions containing the compounds, and methods of controlling insects and mites using the compounds.

BACKGROUND OF THE INVENTION

There is an acute need for new insecticides and acaricides. Insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore a need exists for new insecticides and acaricides, and particularly for compounds that have new or atypical modes of action.

A number of 3,5-diphenyl-1H-1,2,4-triazole derivatives have been described in the literature as having acaricidal activity. U.S. Pat. No. 5,482,951; JP 8092224, EP572142, JP 08283261. To applicants knowledge, however, none of these compounds has become a commercial product. Nitro furanyl triazoles are described by L. E. Benjamin and H. R. Snyder as antimicrobials (*J. Heterocyclic Chem.* 1976, 13, 1115) and by others as antibacterials (*J. Med. Chem.* 1973, 16(4), 312–319; *J. Med. Chem.* 1974, 17(7), 756–758). The present invention provides novel compounds with commercial level activity against mites and insects.

SUMMARY OF THE INVENTION

This invention provides novel compounds especially useful for the control of insects and mites.

More specifically, the invention provides novel insecticidally active compounds of the formula (1)

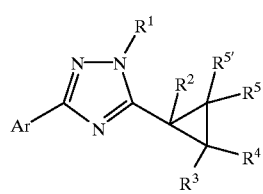

(1)

wherein
Ar is a group of the formula

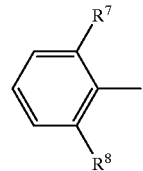

wherein $R^7$ and $R^8$ are independently H, Cl, F, methyl, halomethyl, methoxy, or halomethoxy;

$R^1$ is lower alkyl, haloalkyl, lower alkenyl, lower alkynyl, or benzyl;

$R^2$ is H, Cl, Br, lower alkyl, lower alkenyl, lower alkynyl, alkoxyalkyl;

$R^3$ is selected from H, halo, lower alkyl, ($C_7$–$C_{21}$) straight chain alkyl, hydroxy, lower alkoxy, haloalkyl, haloalkoxy, alkoxyalkyl, alkoxyalkoxy, lower alkenyl, haloalkenyl, CN, $NO_2$, $CON(R^6)_2$, ($C_3$–$C_6$) cycloalkyl, $S(O)_m R^6$, SCN, pyridyl, substituted pyridyl, isoxazolyl, substituted isoxazolyl, naphthyl, substituted naphthyl, phenyl, substituted phenyl, —$(CH_2)_n R^6$, —CH=$CHR^6$, —C≡$CR^6$, —$CH_2 SR^6$, —$CH_2 NR^6 R^6$, —$OCH_2 R^6$, —$SCH_2 R^6$, —$NR^6 CH_2 R^6$,

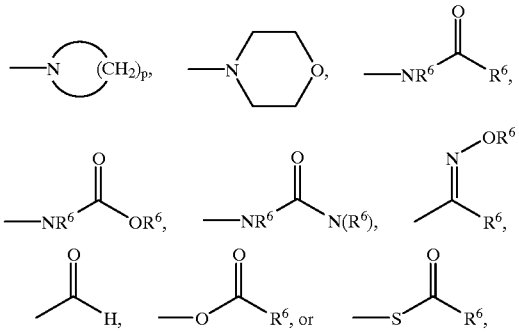

provided one of $R^2$ and $R^3$ is other than H;

$R^4$, $R^5$, and $R^{5'}$ are independently H, halo, lower alkyl, lower alkoxy, haloalkyl, haloalkoxy, CN, $CO_2 R^6$, $CON(R^6)_2$, or $S(O)_m$ alkyl, or $R^4$ and $R^5$, or $R^2$ and $R^5$ form a 5 or 6 member saturated or unsaturated carbocyclic ring which may be substituted by 1 or 2 halo, lower alkyl, lower alkoxy or haloalkyl groups; or $R^6$ is H, lower alkyl, haloalkyl, lower alkenyl, lower alkynyl, phenyl, or substituted phenyl;

m is 0, 1, or 2; and n is 1 or 2;

p is an integer from 2 to 6;

or a phytologically acceptable acid addition salt thereof.

Preferred compounds of formula (1) include the following classes:

(1) Compounds of formula (1) wherein $R^7$ and $R^8$ are independently F or Cl.

(2) Compounds of formula (1) wherein $R^7$ and $R^8$ are both F.

(3) Compounds of formula (1) wherein $R^7$ and $R^8$ are both Cl.

(4) Compounds of formula (1) wherein $R^7$ is F and $R^8$ is Cl.

(5) Compounds of formula (1), and particularly compounds of class (1), (2), (3), or (4) as defined above, wherein $R^2$ is H, $CH_3$, Br, or substituted phenyl.

(6) Compounds of class (5) wherein $R^2$ is $CH_3$.

(7) Compounds of formula (1), and particularly compounds of any one of classes (1) through (6) defined above, wherein $R^3$, $R^4$, and $R^5$ are independently selected from H, halo, methyl, and methoxy.

(8) Compounds of formula (1), and particularly compounds of any one of classes (1) through (7) as defined above, wherein $R^5$ and $R^{5'}$ are both H.

(9) Compounds of formula (1) wherein $R^2$ is $CH_3$, $R^3$ and $R^4$ are Cl, and $R^5$ and $R^{5'}$ are H.

The invention also provides new processes and intermediates for preparing compounds of formula (1) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

The term "lower alkyl" refers to ($C_1$–$C_6$) straight hydrocarbon chains and ($C_3$–$C_6$) branched and cyclic hydrocarbon groups.

The terms "lower alkenyl" and "lower alkynyl" refer to ($C_2$–$C_6$) straight hydrocarbon chains and ($C_3$–$C_6$) branched hydrocarbon groups containing at least one double or triple bond, respectively.

The term "lower alkoxy" refers to -O-lower alkyl.

The terms "halomethyl", "haloalkyl", and "haloalkenyl" refer to methyl, lower alkyl, and lower alkenyl groups substituted with one or more halo atoms.

The terms "halomethoxy" and "haloalkoxy" refer to methoxy and lower alkoxy groups substituted with one or more halo atoms.

The term "alkoxyalkyl" refers to a lower alkyl group substituted with a lower alkoxy group.

The term "alkoxyalkoxy" refers to a lower alkoxy group substituted with a lower alkoxy group.

The terms "substituted naphthyl", "substituted thienyl," "substituted pyrimidyl," "substituted pyrazolyl," "substituted pyridyl," and "substituted isoxaxolyl" refer to the ring system substituted with one or more groups independently selected from halo, halo ($C_1$–$C_4$) alkyl, CN, $NO_2$, ($C_1$–$C_4$) alkyl, ($C_3$–$C_4$) branched alkyl, phenyl, ($C_1$–$C_4$) alkoxy, or halo ($C_1$–$C_4$) alkoxy.

The term "substituted phenyl" refers to a phenyl group substituted with one or more groups independently selected from halo, ($C_1$–$C_{10}$) alkyl, branched ($C_3$–$C_6$) alkyl, halo ($C_1$–$C_7$) alkyl, hydroxy ($C_1$–$C_7$) alkyl, ($C_1$–$C_7$) alkoxy, halo ($C_1$–$C_7$) alkoxy, phenoxy, phenyl, $NO_2$, OH, CN, ($C_1$–$C_4$) alkanoyl, benzoyl, ($C_1$–$C_4$) alkanoyloxy, ($C_1$–$C_4$) alkoxycarbonyl, phenoxycarbonyl, or benzoyloxy.

Unless otherwise indicated, when it is stated that a group may be substituted with one or more substituents selected from an identified class, it is intended that the substituents may be independently selected from the class.

Synthesis

Compounds of formula (1) can be prepared by the method illustrated in Scheme I:

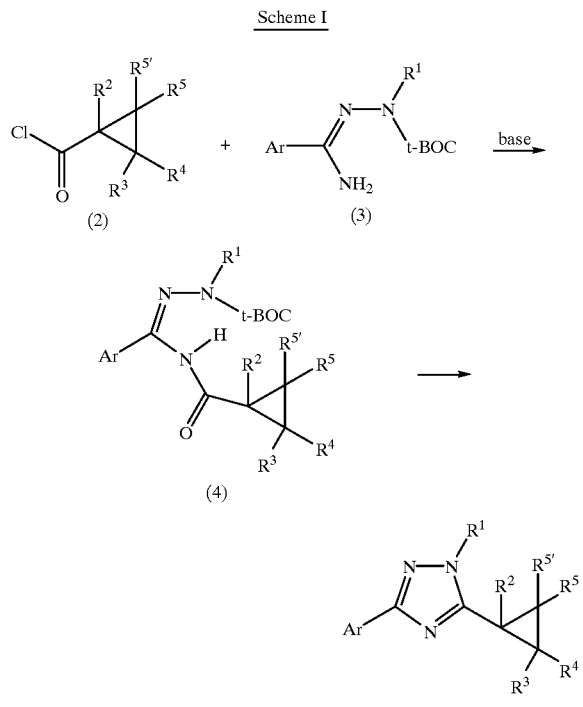

wherein Ar and $R^1$ through $R^{5'}$ are as defined in formula (1) above. The sequence shown in Scheme 1 involves the coupling of cyclopropyl acid chlorides of formula (2) with the amidrazone of formula (3). Preparation 1, hereinafter, illustrates preparation of an amidrazone of formula (3). The base used in the coupling could be any organic or inorganic base. Cyclopropyl acid chlorides of formula (2) are prepared from corresponding cyclopropyl carboxylic acids of formula (5)

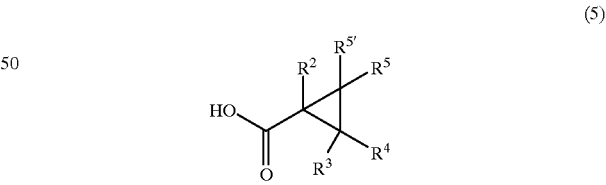

which are either commercially available or are readily made through known procedures. A good general method is the dihalocarbene insertion into activated olefins as outlined in Acta. *Chem. Scandinavica* B31, (1977) 823–825 and *Chem. Ber.* 109, 2351–2369 1976. Conversion of carboxylic acids of formula (5) to the corresponding acid chlorides of formula (2) is carried out by conventional methods, as illustrated hereinafter in Preparation 3. Intermediates of formula (4) can be isolated or not and the entire sequence can be done in one pot as seen in Example 1, hereinafter.

Preparation 1
The following steps illustrate preparation of the amidrazone of formula (3a)

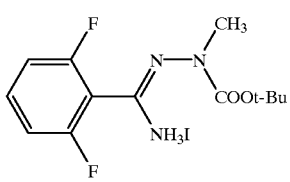

(3a)

A. 2,6-difluorobenzenethioamide

Into a 3 L three necked round bottom flask equipped with a mechanical stirrer, dry ice condenser, dropping funnel, and outlet to a trap filled with bleach was added pyridine (550 mL), 2,6-difluorobenzonitrile (208 g, 1.50 mol), triethylamine (202 g, 279 mL, 2.0 mol), and sodium sulfide hydrate (521 g, 2.17 mol) broken into pieces small enough to fit into the flask. The temperature of the stirred mixture was lowered to approximately 5° C. and to the slurry was added dropwise concentrated hydrochloric acid (143 g, 288 mL, 3.99 mol). An exotherm was noted and the rate of addition of the hydrochloric acid was such that the temperature of the reaction mixture did not exceed 25° C. for a total addition time of 75 min. The cooling bath was removed and the slurry was allowed to warm to RT and to stir over night. The mixture was poured into water (2 L) and was extracted with ether (3×500 mL). The ether layer was washed with dilute sulfuric acid, water, brine, dried (MgSO$_4$), and the solvent removed in vacuo to give 232 grams of crude product. The starting material was removed from the product via kugelrohr distillation to give 197 g (76%) of 2,6-difluorobenzenethioamide. This material was used without further purification.

B. S-methylthio-2,6-difluorobenzamidinium iodide

Into a 3 L three necked flask equipped with a mechanical stirrer and dropping funnel was added acetone (1150 mL) and 2,6-difluorobenzenethioamide (197 g, 1.14 mol). The temperature of the stirred solution was lowered to approximately 5° C. and iodomethane (161 g, 70.6 mL, 1.14 mol) was added dropwise. The ice bath was removed and the slurry was allowed to stir over night. The resulting yellow solids were removed via filtration and washed with ether to obtain 223 grams. An additional portion of material was obtained from the filtrate by removal of the solvent in vacuo. Ether was added to the residue and the resulting solids removed via filtration to obtain an additional 57 grams of material. The combined solids totaled 280 g (77.9% yield) of S-methylthio-2,6-difluoro-benzimidinium iodide: mp 168–169° C.; $^1$H NMR (DMSO-d$_6$)δ7.7 (m, 1H), 7.4 (m, 2H), 2.7 (s, 3H).

C. N-tert-butoxycarbonyl-N-methylhydrazine

Into a 1 L three necked round bottom flask equipped with a mechanical stirrer and dropping funnel was added methyl hydrazine (42.2 g, 0.916 mol) and THF (100 mL). The temperature of the mixture was cooled to 5° C. and a solution of di-tert-butyl dicarbonate (100 g, 0.458 mol) dissolved in THF (150 mL) was added dropwise. The cooling bath was removed and the mixture was stirred at RT overnight. The liquid was decanted from a gummy precipitate and the solvent removed in vacuo to give approximately 70 grams of a clear liquid. The gummy precipitate was partitioned between methylene chloride and water. The methylene chloride layer was washed with brine, dried (Na$_2$SO$_4$) and the solvent removed in vacuo. The resulting residue was combined with that from the previous evaporation and distilled at approximately 20 mm Hg (bp 77–78° C.) to give 40.2 g (60% yield) of N-tert-butoxycarbonyl-N-methylhydrazine: $^1$H NMR (CDCl$_3$) δ4.1 (s, b, 2H), 3.05 (s, 3H), 1.5 (s, 9H).

D. Amidrazone of formula (3a)

Into a 1 L round bottom flask equipped with a mechanical stirrer, dropping funnel, and outlet to a trap filled with bleach, was added S-methyl-2,6-difluorobenziminium iodide (63.8 g, 0.202 mol) and methanol (180 mL). To the stirred solution was added dropwise N-tert-butoxycarbonyl-N-methylhydrazine (29.6 g. 0.202 mol). The solution was allowed to stir overnight and the methanol was removed in vacuo. The residue was triturated with ether and the solids removed via filtration to give 66.3 grams (79.0% yield) of the amidrazone of formula (3a) : mp 172–173° C. (dec); $^1$H NMR (DMSO-d$_6$) δ12.3 (s, b, 1H), 10.4 (d, b, 2H), 7.9 (m, 1H), 7.4 (m, 2H), 3.1 (s, 3H), 1.5 (s, 9H).

EXAMPLE 1

3-(2,6-difluorophenyl)-5-(2,2-dichloro-1-methyl-cyclopropane)-1-methyl-1H-1,2,4-triazole N-methyl-N-t-butoxycarbony-2,6-difluorophenylamidrazone (5.9 mmol., 1.68 g.), 2,2-dichloro-1-methyl-cyclopropanecarbonyl chloride (5.9 mmol., 1.106 g.), and potassium carbonate (5.9 mmol., 0.814 g.) were combined in toluene (60 ml.) and refluxed overnight. Solvent was removed. Chromatography (SiO$_2$, 5–10% EtOAc–CH$_2$Cl$_2$) afforded the product as a white solid (260 mg., 0.82 mmol., 14% yield). MP 77–80° C.

1H NMR (m, 7.35 ppm, 1H; m 6.99 ppm, 2H; s, 4.08 ppm, 3H; d, 2.46 ppm, 1H; s, 1.75 ppm, 3H; d, 1.57 ppm, 1H). Elemental Analysis ( Carbon, calc. 49.07, Fd. 48.88; Hydrogen, calc. 3.49, Fd. 3.52; Nitrogen, calc. 13.21, Fd. 12.89)

Another route to intermediates of formula (4) is shown in Scheme 2.

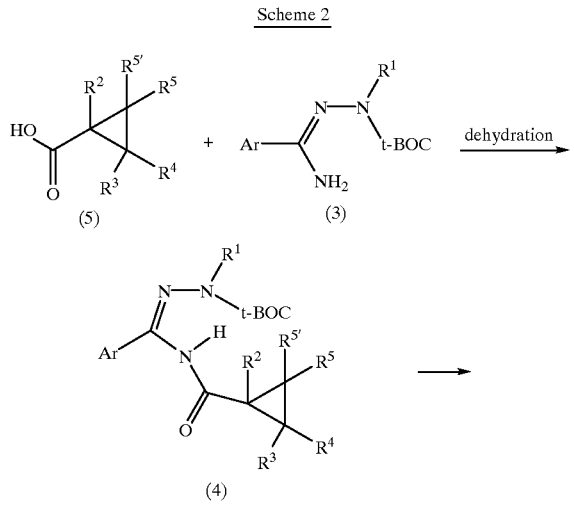

-continued

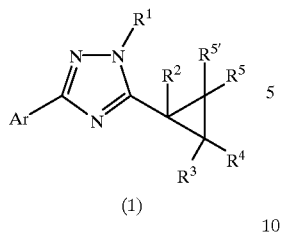

(1)

wherein R¹ through R⁵ ' are as defined in formula (1) above. The coupling is done with a dehydrating agent such as 1,3-dicyclohexylcarbodiimide. The coupling, isolation of the intermediate, and subsequent deprotection and ring closure are illustrated in Examples 2 and 3 below.

Preparation 2

2,2-Dibromo-1-methylcyclopropanecarboxylic Acid, Methyl Ester

To a solution of methyl methacrylate (3.15 g, 31.6 mmol), benzyltriethylammonium chloride (TEBA) (0.72 g, 10 mol %), in 12.6 mL of 50% sodium hydroxide solution was added bromoform (15.95 g, 63 mmol). The reaction was stirred overnight and then extracted with dichloromethane (2×25 mL). The organic extracts were washed with brine, dried (MgSO₄), and then condensed in vacuo. The residue was purified by bulb to bulb distillation to give 6.5 g of the known product as an oil. $^1$H NMR (CDCl₃) δ3.8 (s, 3H), 2.4(d, 1H), 1.6 (s, 3H), 1.5 (d, 1H).

Preparation 3

2,2-Dibromo-1-methylcyclopropanecarboxylic Acid

To 25 mL of a 50:50 mixture of tetrahydrofuran/water was added 2,2-dibromo-1-methylcyclopropanecarboxylic acid, methyl ester(2.72 g, 10 mmol)and lithium hydroxide (0.8 g, 20 mmol). The reaction mixture was stirred overnight. The reaction mixture was acidified with 1 M hydrochloric acid (24 mL). The reaction mixture was extracted with dichloromethane (2×25 mL) and the organic phases were collected, washed with brine, dried (MgSO₄)and evaporated to give the title product (16 g) as white crystals mp 108–109° C.

EXAMPLE 2

(6)

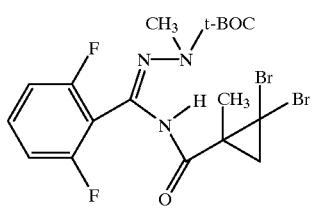

To a solution of the amidrazone of Preparation 1 (1.28 g, 4.5 mmol), 1,3-dicyclohexylcarbodiimide (1 M solution in dichloromethane) (5 mL, 5 mmol), N,N-dimethylaminopyridine (55 mg, 0.5 mmol), in dichloromethane was added 2,2-dibromo-1-methylcyclopropanecarboxylic acid (1.16 g, 4.5 mmol). The reaction mixture was stirred overnight, then filtered, and then evaporated. The residue was chromatographed on silica gel (hexanes/ ethyl acetate 5:95 to 50:50). The product fractions were collected and the solvent removed in vacuo to give the desired product (444 mg) as an oil. $^1$H NMR (CDCl₃) δ9.4(br s, 1H), 7.3(m, 1H), 6.9 (m, 2H), 3.3(s, 3H), 2.3 (d, 1H) 1.7 (s, 3H), 1.6 (s, 9H) 1.5 (d, 1H).

EXAMPLE 3

3-(2,6-difluorophenyl)-5-(2,2-dibromo-1-methyl-cyclopropane)-1-methyl-1H-1,2,4-triazole (7)

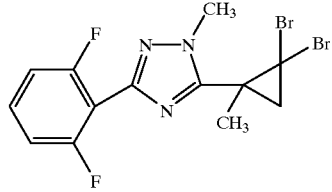

To a solution of a 3/1 mixture of dichloromethane/trifluoroacetic acid (4 mL) at 0° C. was added the product of Example 2 (525 mg, 1 mmol) in 1 mL of dichloromethane. The reaction was allowed to come to room temperature, and was stirred overnight. The reaction mixture was neutralized with saturated sodium bicarbonate solution. The reaction mixture was extracted with dichloromethane. The organic phase was dried (MgSO₄). The solvent was evaporated to give 313 mg of the desired product as white crystals, mp 101–102 Elemental Analysis (Carbon, calc.38.36, Fd. 36.45; Hydrogen, calc. 2.72, Fd. 2.68; Nitrogen, calc. 10.32, Fd. 10.20). $^1$H NMR (CDCl₃) δ7.3 (m 1H), 7.0 (m, 2H), 4.0 (s, 3H), 2.6 (d, 1H), 1.9 (s, 1H), 1.7 (m, 4H).

Another method for preparing compounds of formula (1) is illustrated in Scheme 3:

Scheme 3

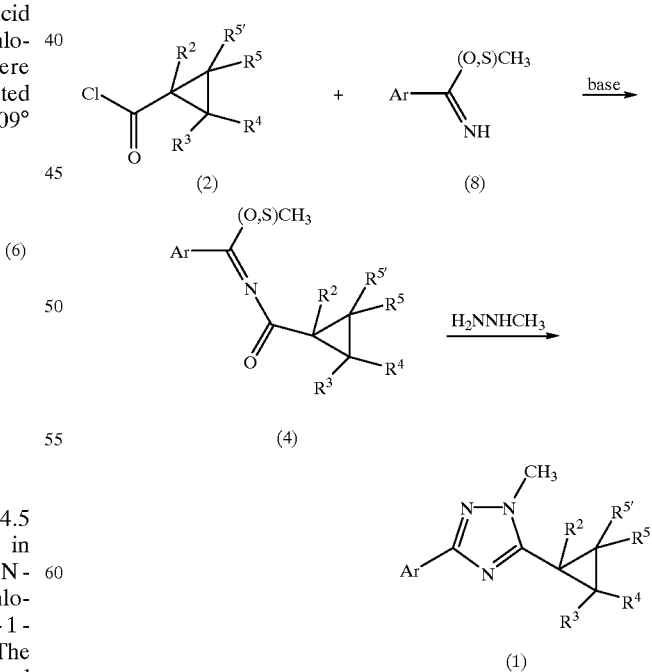

wherein R² to R⁵' are as defined in formula (1). Aryl acyl(thio)imidates of type (8) are known in the literature and can be used as their acid addition salt. In this case, tetrafluoroboric acid, hydrogen chloride, hydrogen bromide, hydrogen iodide, or the like, may be used. Aryl acylimidates are available through the nitrile, as illustrated in J. Org. Chem. Vol. 33, p.1679, 1968, and are also available through a process outlined in U.S. Pat. No. 4,025,504. Thioimidates are readily available through alkylation of the corresponding thioamides which are themselves commercially available or can be made from the amide (Phosphorus Sulfur (1985), 25(3), 297–305) or nitrile (Chem.-Ztg. (1980), 104(12), 365–7); J. Chem. Soc. (1952), 742; Can. J. Chem. (1985), 63, 3075).

Reaction of the cyclopropyl acid chloride (2) and the imidate (8) to give the adduct (4) can generally be accomplished in any inert solvent with any organic or inorganic base.

Reaction of compounds such as (4) with methyl hydrazine gives the titled triazoles, generally in good yield with a high degree of regiospecificity. A specific example of this reaction is given in Synthesis, 483 (1983).

This procedure is illustrated in the following Examples 4 and 5.

EXAMPLE 4

3-(2,6-difluorophenyl)-5-(2,2-dichloro-1-methyl-cyclopropane)-1-methyl-1H-1,2,4-triazole To a 50 mL one necked round bottom flask equipped with a magnetic stirrer and condenser under an atmosphere of nitrogen was added 2,2-dichloro-1-methyl cyclopropane carboxylic acid (0.42 g, 3 mmol), 1,2-dichloroethane(20 mL), thionyl chloride (0.53 g, 0.32 mL, 4.5 mmol) and several drops of DMF. The mixture was allowed to reflux for 3 hr and the solvent was removed in vacuo and placed onto a vacuum pump to a constant weight. To a three necked flask equipped with a condenser and containing methyl 2,6-difluorobenzthioimidate (0.94 g, 3.0 mmol), and triethylamine (0.2 g, 2.0 mmol), and toluene (20 mL) was added dropwise 2,2-dichloro-1-methylcyclopropyl carboxyl chloride dissolved in toluene (10 mL). The mixture was brought to the point of reflux and maintained at that temperature for 3 hr. To the refluxing mixture was added methyl hydrazine (0.86 g, 18 mmol) dissolved in toluene was added dropwise. The mixture was allowed to reflux for 1 hr and GC analysis showed (4)(51.3% as the major product). GC/MS at 15.6 min for masses 317/319. Column chromatographic purification of the crude product gave 0.62 g (65% yield) of(4): 97% pure by GC analysis; $^1$H NMR (CDCl$_3$) δ7.4 (m 1H), 7.0 (m, 2H), 4.05 (s, 3H), 2.4 (d, 1H), 1.7 (m, 4H).

EXAMPLE 5

3-(2-chloro-6-fluorophenyl)-5-(2,2-dichloro-1-methylcyclopropane)-1-methyl-1H-1,2,4-triazole

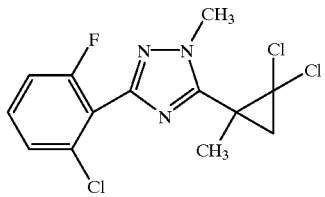

(9)

To a suspension of 2-chloro-6-fluorobenzthioimidate iodide (14.92 g,45 mmol)in 300 mL of dry toluene was added triethylamine (18 g, 180 mmol) then 2,2-dichloro-1-methylcyclopropyl carboxyl chloride (8.44 g, 45 mmol) dropwise. The mixture was refluxed for 2 hours. Methyl hydrazine (12.44 g, 180 mmol) was added dropwise at 100° C. the reaction mixture was refluxed for an additional hour then stirred at room temperature overnight. The reaction mixture was washed with 2N NaOH (2×150 mL), with 2N HCl, brine, and then dried (Na$_2$SO$_4$). The solvent was evaporated and the residue was chromatographed on silica gel (hexanes/ethyl acetate, 10:90 to 15:85 to give the product (9.25 g) as white crystals, mp 106–108.

The compounds identified in the following Table 1 were prepared using the procedures illustrated in the foregoing examples, and the compounds were tested against cotton aphid, two-spotted spider mite and sweetpotato whitefly using procedures described hereinafter.

TABLE 1

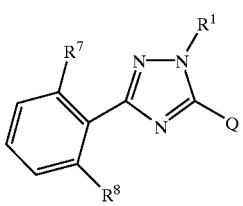

| cmpd no. | R$^7$ | R$^8$ | R$^1$ | Q | mp °C. | CA$^†$ | TSSM$^‡$ | WF* |
|---|---|---|---|---|---|---|---|---|
| * | Cl | H | CH$_3$ | ![cyclopropyl-CH3] | oil | F | F | F |
| 1 | F | F | CH$_3$ | ![cyclopropyl-CH3,Cl,Cl] | 77–80 | A | A | F |

TABLE 1-continued

| cmpd no. | R⁷ | R⁸ | R¹ | Q | mp °C. | CA† | TSSM‡ | WF* |
|---|---|---|---|---|---|---|---|---|
| 2 | F | F | $CH_3$ | 1-methyl-cyclopropyl-p-ClPh | oil | A | A | G |
| 3 | F | F | $CH_3$ | 2-methyl-cyclopropyl-Ph | oil | B | A | |
| 4 | F | F | $CH_3$ | 1,2,2-trimethyl-3-(2-methylprop-1-enyl)cyclopropyl | 78–79 | F | A | |
| 5 | F | F | $CH_3$ | cyclopropyl | 104–106 | A | A | G |
| 6 | F | F | $CH_3$ | 1,1-dimethylcyclopropyl | oil | B | A | E |
| 7 | F | F | $CH_3$ | 1-methyl-2,2-dichlorocyclopropyl | 93–97 | A | A | F |
| 8 | Cl | F | $CH_3$ | 1,2-dimethyl-2,2-dichlorocyclopropyl | 105–109 | A | A | A |
| 9 | F | F | $CH_3$ | 1-methyl-2-bromocyclopropyl | 62–64 | A | A | F |
| 10 | F | F | $CH_3$ | 1,2-dimethyl-2,2-dibromocyclopropyl | 101–102 | A | A | A |
| 11 | Cl | Cl | $CH_3$ | 1,2-dimethyl-2,2-dichlorocyclopropyl | 122–124 | C | A | A |
| 12 | Cl | F | $CH_3$ | 1,2-dimethyl-2,2-dibromocyclopropyl | 113–114 | A | A | C |

TABLE 1-continued

| cmpd no. | R⁷ | R⁸ | R¹ | Q | mp °C. | CA† | TSSM‡ | WF* |
|---|---|---|---|---|---|---|---|---|
| 13 | F | F | CH₃ | (7,7-dichloro-1-methylbicyclo[4.1.0]heptane) | 93–95 | B | A | G |
| 14 | F | F | CH₃ | (2,2-difluoro-1,1-dimethylcyclopropyl) | 79–80 | F | B | |
| 15 | F | F | CH₃ | (2,2-dichloro-1,3,3-trimethylcyclopropyl) | 74–75 | C | A | G |
| 16 | F | F | CH₃ | (2,2-dichloro-1,3,3-trimethylcyclopropyl, stereo) | 87 | B | | |
| 17 | F | F | CH₃ | (2-chloro-2-fluoro-1,1-dimethylcyclopropyl) | oil | B | A | G |
| 18 | Cl | F | CH₃ | (2-bromo-2-chloro-1,1-dimethylcyclopropyl) | 129–130 | A | A | A |
| 19 | F | F | CH₃ | (2-bromo-2-fluoro-1,1-dimethylcyclopropyl) | 79–98 | B | A | E |
| 20 | Cl | F | CH₃ | (2,2-difluoro-1,1-dimethylcyclopropyl) | oil | A | A | C |
| 21 | F | F | CH₃ | (2,2,3-trichloro-1-methylcyclopropyl) | 76–78 | A | A | C |

TABLE 1-continued

| cmpd no. | R⁷ | R⁸ | R¹ | Q | mp °C. | CA† | TSSM‡ | WF* |
|---|---|---|---|---|---|---|---|---|
| 22 | Cl | F | CH₃ | (2-methyl-1,1-dichloro-cyclopropyl with additional Cl) | 76–78 | A | A | C |
| 23 | Cl | F | CH₃ | (trans-2-methyl-2-chlorocyclopropyl) | 94–96 | B | A | F |
| 24 | F | F | CH₃ | (2-methyl-2-chlorocyclopropyl, H) | 85–87 | A | A | F |
| 25 | F | F | CH₃ | (2,2-dimethyl-bromocyclopropyl) | 92 | A | A | |
| 26 | Cl | F | CH₃ | (2,2-dimethylcyclopropyl, CH₃) | 90–92.5 | C | A | G |
| 27 | Cl | F | CH₃ | (2-ethyl-1,1-dichlorocyclopropyl) | 116–119 | A | A | G |
| 28 | Cl | CH₃ | CH₃ | (2-methyl-1,1-dichlorocyclopropyl) | oil | A | A | A |
| 29 | F | F | CH₃ | (2,2-dimethyl-1-CO₂CH₃-1-Cl cyclopropyl) | 127 | A | | G |
| 30 | F | F | CH₃ | (2,2-dimethyl-1-CO₂CH₃-1-Cl cyclopropyl, trans) | 123 | A | A | G |
| 31 | F | F | CH₃ | (2-methyl-2-CN-1-Cl cyclopropyl) | | A | C | G |
| 32 | F | Cl | CH₃ | (2,2,3,3-tetramethylcyclopropyl) | 104–105 | B | | G |

TABLE 1-continued

| cmpd no. | R⁷ | R⁸ | R¹ | Q | mp °C. | CA† | TSSM‡ | WF* |
|---|---|---|---|---|---|---|---|---|
| 33 | F | CF₃ | CH₃ | cyclopropyl: CH₃, Cl, Cl | 105–107 | B | E | G |
| 34 | F | F | CH₃ | cyclopropyl: H₃C, Cl, CF₃ | 164–165 | A | A | G |
| 35 | F | F | CH₃ | cyclopropyl: H₃C, CH₂Cl, Cl | | D | | |
| 36 | F | F | CH₃ | cyclopropyl: H₃C, Cl, CN | 172 | A | A | G |
| 37 | F | F | CH₃ | cyclopropyl: H₃C, CF₃, Cl | oil | A | | G |
| 38 | F | F | CH₂Br | cyclopropyl: CH₃, Cl, Cl | | A | B | G |
| 39 | F | F | CH₂OCH(CH₃)₂ | cyclopropyl: CH₃, Cl, Cl | 77 | F | G | G |
| 40 | F | F | CH₂OC₃H₇ | cyclopropyl: CH₃, Cl, Cl | 98 | E | A | G |
| 41 | F | Cl | C₂H₅ | cyclopropyl: CH₃, Cl, Cl | 92 | A | A | G |
| 42 | F | Cl | CH₂CF₃ | cyclopropyl: CH₃, Cl, Cl | 80–87 | C | A | C |
| 43 | F | Cl | cyclohexyl | cyclopropyl: CH₃, Cl, Cl | 119–120 | F | A | A |

TABLE 1-continued

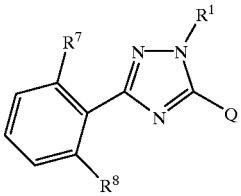

| cmpd no. | R⁷ | R⁸ | R¹ | Q | mp °C. | CA† | TSSM‡ | WF* |
|---|---|---|---|---|---|---|---|---|
| 44 | F | Cl | $CH_2Cl$ | 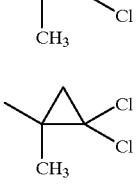 | 95 | | A | G |
| 45 | F | Cl | $C_3H_7$ | 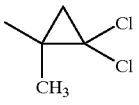 | 84–86 | A | A | B |
| 46 | F | Cl | $C_4H_9$ | 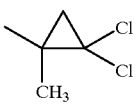 | 58–60 | D | A | A |
| 47 | F | Cl | benzyl | | 101 | A | | G |

*Comparative Compound 88 from U.S. Pat. No. 5,466,705.
CA† refers to activity at 50 ppm against cotton aphid,
TSSM‡ refers to activity at 100 ppm against two-spotted spider mite, and
WF* refers to activity at 200 ppm against whitefly.

In each case the rating scale is as follows

| % Control | Rating |
|---|---|
| 91–100 | A |
| 81–90 | B |
| 71–80 | C |
| 61–70 | D |
| 51–60 | E |
| less than 51 | F |
| inactive | G |

Insecticide and Miticide Utility

The compounds of the formulae (1) are suitable for controlling pests on animals and plants. Such pests belong mainly to the arthropod family, such as, especially, insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera, and arachnids of the order Acarina, such as, for example, mites, aphids, and ticks.

Therefore, the present invention also is directed to a method for inhibiting an insect, mite, or aphid which comprises applying to a locus of the insect or mite an insect- or mite-inhibiting amount of a compound of formula (1).

The compounds are useful for reducing populations of insects and mites and are useful in a method of inhibiting an insect or mite population which comprises applying to a locus of the insect or mite an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant parts that the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites, or a decrease in the number of viable insect or mite eggs. The extent of reduction accomplished by a compound depends, of course, upon the application rate of the compound, the particular compound used, and the target insect or mite species. At least an inactivating amount should be used. The terms "insect-inactivating amount" and "mite-inactivating amount" are used to describe the amount, which is sufficient to cause a measurable reduction in the treated insect or mite, population. Generally an amount in the range from about 1 to about 1000 ppm active compound is used.

In a preferred embodiment, the present invention is directed to a method for inhibiting a mite or aphid which comprises applying to a plant an effective mite- or aphid-inactivating amount of a compound of formula (1).

Insecticidal test for cotton aphid (*Aphis gossypii*)

To prepare spray solutions, 1 mg of each test compound was dissolved into 1 mL of a 90:10 acetone:ethanol solvent.

This 1 mL of chemical solution was added to 19 mL of water containing 0.05% Tween 20 surfactant to produce a 50 ppm spray solution.

Squash cotyledons were infested with cotton aphid (all life stages)16–20 hours prior to application of spray solution. The solution was sprayed on both sides of each infested squash cotyledon (0.5 mL×2 each side) with a sweeping action until runoff. The plants were allowed to air dry and held for 3 days in a controlled room at 26° C. and 40% RH after which time the test was graded. Grading was by actual count using a dissecting microscope and comparison of test counts to the untreated check. Results are given in Table 1 as percent control based on population reduction versus the untreated.

Insecticidal test for two-spotted spider mite
(*Tetranychus urticae*)
Ovicide Method:

Ten adult female two-spotted spider mites were placed on eight 2.2 cm leaf discs of cotton leaf, allowed to oviposit over 24 hours, and thereafter removed. The leaf discs were sprayed with 100 ppm test solutions using a hand syringe, then allowed to dry with sixteen discs left untreated as a negative control. Discs were placed on an agar substrate and held at 24 C. and 90% relative humidity for 6 days. Percent control based on the number of hatched larvae on treated discs and the number on untreated discs is reported in Table 1.

Evaluation of Tests Compounds on Sweetpotato Whitefly (*Bemisia tabacia*) Under Laboratory Conditions Four mg of each test compound was dissolved by adding 4 ml of a 90:10 acetone:ethanol solvent mixture to the vial containing the sample compound. This solution was added to 16 ml of water containing 0.05% Tween 20 surfactant to produce 20 ml of an 200 ppm spray solution.

Five-week-old cotton plants reared in a greenhouse were stripped of all foliage except for the two uppermost true leaves that were greater than 5 cm in diameter. These plants were then placed into a laboratory colony of whiteflies for two days for oviposition by the colony females. All whiteflies were then removed from the test plants with pressurized air. The spray solution was then applied to the test plants with a hand-held syringe fitted with hollow cone nozzle. One mL spray solution was applied to each leaf top and bottom for a total of 4 mL per plant. Four replications of each test compound utilized a total of 16 mL spray solution. Plants were air dried and then placed in a holding chamber (28° C. and 60% RH) for 13 days. Compound efficacy was evaluated by counting, under an illuminated magnifying glass, the number of large nymphs (3rd-4th instar) per leaf.

Percent control based on reduction of large nymphs of a test compound compared to solution-only (no test compound) sprayed plants is reported in Table 1.

Compounds of the invention have demonstrated activity against green leaf hopper and brown plant hopper.

In addition to being effective against mites, aphids, and insects when applied to foliage, compounds of formula (1) have systemic activity. Accordingly, another aspect of the invention is a method of protecting a plant from insects which comprises treating plant seed prior to planting it, treating soil where plant seed is to be planted, or treating soil at the roots of a plant after it is planted, with an effective amount of a compound of formula (1).

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects, mites, and aphids is not critical and can readily be determined by those skilled in the art in view of the examples above. In general, concentrations of from 10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 5–20 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention are typical of compositions useful in the practice of the present invention.

A. 0.75 Emulsifiable Concentrate

| | |
|---|---|
| Compound of formula (1) | 9.38% |
| "TOXIMUL D" (nonionic/anionic surfactant blend | 2.50% |
| "TOXIMUL H" (nonionic/anionic surfactant blend | 2.50% |
| "EXXON 200" (naphthalenic solvent | 85.62% |

B. 1.5 Emulsifiable Concentrate

| | |
|---|---|
| Compound of formula (1) | 18.50% |
| "TOXIMUL D" | 2.50% |
| "TOXIMUL H" | 2.50% |
| "EXXON 200" | 76.50% |

C. 1.0 Emulsifiable Concentrate

| | |
|---|---|
| Compound of formula (1) | 12.5% |
| N-methylpyrrolidone | 25.00% |
| "TOXIMUL D" | 2.50% |
| "TOXIMUL H" | 2.50% |
| "EXXON 200" | 57.50% |

D. 1.0 Aqueous Suspension

| | |
|---|---|
| Compound of formula (1) | 12.00% |
| "PLURONIC P-103" (block copolymer of propylene oxide and ethylene oxide, surfactant | 1.50% |
| "PROXEL GXL" (bio~ide/preservative | .05% |
| "AF-100" (silicon based antifoam agent | .20% |
| "REAX 88B" (lignosulfonate dispersing agent | 1.00% |
| propylene glycol | 10.00% |
| veegum | .75% |
| xanthan | .25% |
| water | 74.25% |

E. 1.0 Aqueous Suspension

| | |
|---|---|
| Compound of formula (1) | 12.50% |
| "MAKON 10" (10 moles ethyleneoxide nonylphenol surfactant | 1.00% |
| "ZEOSYL 200" (silica | 1.00% |
| "AF-100" | 0.20% |
| "AGRIWET FR" (surfactant | 3.00% |
| 2% xanthan hydrate | 10.00% |
| water | 72.30% |

F. 1.0 Aqueous Suspension

| | |
|---|---|
| Compound of formula (1) | 12.50% |
| "MAKON 10" | 1.50% |
| "ZEOSYL 200" (silica | 1.00% |
| "AF-100" | 0.20% |
| "POLYFON H" (lignosulfonate dispersing agent | 0.20% |
| 2% xanthan hydrate | 10.00% |
| water | 74.60% |

G. Wettable Powder

| | |
|---|---|
| Compound of formula (1) | 25.80% |
| "POLYEON H" | 3.50% |
| "SELLOGEN HR" | 5.00% |
| "STEPANOL ME DRY" | 1.00% |
| gum arabic | 0.50% |

-continued

| "HISIL 233" | 2.50% |
|---|---|
| Barden clay | 61.70% |

H. 1.0 Aqueous Suspension

| Compound of formula (1) | 12.40% |
|---|---|
| "TERGITOL 158-7" | 5.00% |
| "ZEOSYL 200" | 1.0% |
| "AF-IG0" | 0.20% |
| "POLYFON H" | 0.50% |
| 2% xanthan solution | 10.00% |
| tap water | 70.90% |

I. 1.0 Emulsifiable Concentrate

| Compound of formula (1) | 12.40% |
|---|---|
| "TOXIMUL D" | 2.50% |
| "TOXIMUL H" | 2.50% |
| "EXXON 200" | 82.60% |

J. Wettable Powder

| Compound of formula (1) | 25.80% |
|---|---|
| "SELLOGEN HR" | 5.00% |
| "POLYFON H" | 4.00% |
| "STEPANOL ME DRY" | 2.00% |
| "HISIL 233" | 3.00% |
| Barden clay | 60.20% |

K. 0.5 Emulsifiable Concentrate

| Compound of formula (1) | 6.19% |
|---|---|
| "TOXIMUL H" | 3.60% |
| "TOXIMUL D" | 0.40% |
| "EXXON 200" | 89.81% |

L. Emulsifiable Concentrate

| Compound of formula (1) | 5 to 48% |
|---|---|
| surfactant or surfactant blend | 2 to 20% |
| Aromatic Solvent or Mixture | 55 to 75% |

We claim:
1. A compound of the formula (1)

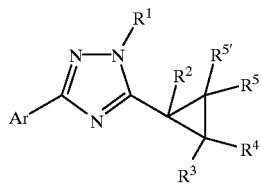

(1)

wherein
Ar is a group of the formula

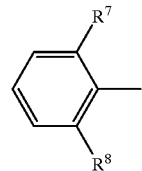

wherein $R^7$ and $R^8$ are independently H, Cl, F, methyl, halomethyl, methoxy, or halomethoxy;
$R^1$ is $CH_3$, $C_2H_5$, $C_3H_7$, $C_4H_9$, $CH_2Br$, $CH_2Cl$, $CH_2CF_3$, cyclohexyl or benzyl;
$R^2$ is $CH_3$;
$R^3$ and $R^4$ are Cl; and
$R^5$ and $R^{5'}$ are H;
or a phytologically acceptable acid addition salt thereof.

2. A compound of claim 1 wherein $R^7$ and $R^8$ are both F, $R^7$ and $R^8$ are both Cl, or $R^7$ is F and $R^8$ is Cl.

3. A composition for controlling insects or mites which comprises a compound of claim 1 in combination with a phytologically-acceptable carrier.

4. A method of controlling insects or mites which comprises applying to a locus where control is desired an insects- or mite-inactivating amount of a compound of claim 1.

* * * * *